(12) United States Patent
Sud

(10) Patent No.: US 9,826,957 B2
(45) Date of Patent: Nov. 28, 2017

(54) DISPOSABLE STETHOSCOPE COVER

(71) Applicant: Shivani Sud, Durham, NC (US)

(72) Inventor: Shivani Sud, Durham, NC (US)

(*) Notice: Subject to any disclaimer, the term of this patent is extended or adjusted under 35 U.S.C. 154(b) by 0 days.

(21) Appl. No.: 15/087,780

(22) Filed: Mar. 31, 2016

(65) Prior Publication Data

US 2016/0287206 A1 Oct. 6, 2016

Related U.S. Application Data

(60) Provisional application No. 62/140,772, filed on Mar. 31, 2015.

(51) Int. Cl.
*A61B 7/02* (2006.01)

(52) U.S. Cl.
CPC ...................... *A61B 7/02* (2013.01)

(58) Field of Classification Search
CPC .......................................................... A61B 7/02
USPC ........................................................ 181/131
See application file for complete search history.

(56) References Cited

U.S. PATENT DOCUMENTS

| | | | |
|---|---|---|---|
| 5,466,898 A | 11/1995 | Gilbert et al. | |
| 5,486,659 A | 1/1996 | Rosenbush | |
| 5,539,162 A * | 7/1996 | Tuttle .................. | A61B 46/10 181/131 |
| 5,592,946 A * | 1/1997 | Eddy .................... | A61B 7/02 150/154 |
| 5,623,131 A * | 4/1997 | Earnest ................ | A61B 7/02 128/DIG. 15 |
| 5,747,751 A | 5/1998 | Weckerle et al. | |
| 6,006,856 A | 12/1999 | Skubal et al. | |
| 6,575,917 B2 | 6/2003 | Giroux et al. | |
| 7,575,094 B1 | 8/2009 | Rosenberg | |
| 7,614,477 B2 | 11/2009 | Statner et al. | |
| 7,806,267 B2 | 10/2010 | Pack-Walden et al. | |
| 2002/0170771 A1 * | 11/2002 | Milam .................. | A61B 7/02 181/131 |
| 2006/0219472 A1 * | 10/2006 | Vance .................. | A45F 5/02 181/131 |
| 2008/0251313 A1 | 10/2008 | Knight et al. | |

(Continued)

FOREIGN PATENT DOCUMENTS

| | | |
|---|---|---|
| JP | 10-033528 | 2/1998 |
| WO | 0149179 A1 | 7/2001 |

OTHER PUBLICATIONS

Creative Med Solutions, ISO—Line Guardian Series, Disposable Stethoscope Covers, www.creativemedsolutions.com.

(Continued)

*Primary Examiner* — Forrest M Phillips
(74) *Attorney, Agent, or Firm* — Michael G. Johnston; Moore & Van Allen PLLC

(57) ABSTRACT

A protective cover for a stethoscope comprises an elongate sleeve member having a closed first end and an open second end. The sleeve member defines an enclosed interior volume accessible via the open second end. A clip member is operatively connected to the first or second ear tube. A head and interconnecting elongate tubular body portion of the stethoscope are reposed in a position in the interior volume of the sleeve member such that the head and the body portion of the stethoscope are substantially covered. The clip member releasably holds the sleeve member in this position.

12 Claims, 1 Drawing Sheet

(56) References Cited

U.S. PATENT DOCUMENTS

2009/0165186 A1 7/2009 Mijares et al.
2009/0288908 A1* 11/2009 Giroux ..................... A61B 7/02
   181/131

OTHER PUBLICATIONS

Thakore, Y.B., Ph.D., New Disposable Stethoscope Covers Could Become as Common as Gloves in Healthcare Facilities, Nov. 4, 2011, http://www.prweb.com/releases/Disposable_Medical_Device/Stethosco . . . .

* cited by examiner

DISPOSABLE STETHOSCOPE COVER

CROSS-REFERENCES

This application is related to U.S. provisional application No. 62/140,772, filed Mar. 31, 2015, entitled "DISPOSABLE STETHOSCOPE COVERS AS A POTENTIAL SOLUTION TO PREVENT STETHOSCOPE CONTAMINATION AND OVERCOME BARRIERS TO STETHOSCOPE HYGIENE", naming Shivani Sud as the inventor. The contents of the provisional application are incorporated herein by reference in their entirety, and the benefit of the filing date of the provisional application is hereby claimed for all purposes that are legally served by such claim for the benefit of the filing date.

BACKGROUND

A protective sleeve is described for enclosing a portion of a medical stethoscope and, more particularly, a stethoscope sleeve for the head and a portion of the tubing of a stethoscope for preventing contamination and transmission of infectious organisms and other biohazards.

Stethoscopes used by health care professionals during patient examinations have become a known cause of cross-contamination and biohazards transmission. The stethoscope, typically a personal device carried by a health care professional, is used to examine multiple patients. During each examination process, the stethoscope directly contacts body parts of each patient. Thus, the stethoscope acts as a fomite from patient to patient, significantly increasing cross-contamination and transmission of infectious organisms.

Cleaning a stethoscope between uses is typically ineffective in eliminating certain resistant infectious organisms. It is also difficult and impractical for health care professionals to carry out the cleaning process each time with consistency. Single-patient use disposable stethoscopes have been implemented as a less than adequate solution to eliminate breaks in barrier protection. The single-patient stethoscopes are used by all providers caring for a given patient resulting in multiple opportunities for the stethoscope ear tips to become contaminated and spread pathogens to the providers resulting in an occupational safety hazard for the providers and increased risk of pathogen transmission to patients.

For the foregoing reasons, there is a need for a new stethoscope sleeve for preventing contact with the stethoscope thereby reducing the chances for contamination and transmission of infection from one observed patient or health care worker to another worker or patient. The sleeve should cover at least a portion of the body of the stethoscopes for providing the necessary protection while not interfering with the stethoscope's operation. Ideally, means for releasably retaining the sleeve on the stethoscope is also provided.

SUMMARY

A protective cover is provided for a stethoscope including a head, first and second ear tubes, and an elongate tubular body portion extending between and interconnecting the head and the ear tubes. The protective cover comprises an elongate sleeve member having a closed first end and an open second end. The sleeve member defines an enclosed interior volume accessible via the open second end. A clip member is adapted to be operatively connected to the first or second ear tube. The head and the interconnecting elongate tubular body portion of the stethoscope are reposed in a position in the interior volume of the sleeve member such that the head and the body portion of the stethoscope are substantially covered. The clip member releasably holds the sleeve member in the position.

A protectively covered stethoscope assembly is also provided and comprises a stethoscope including a head, first and second ear tubes, and an elongate tubular body portion extending between and interconnecting the head and the ear tubes. An elongate sleeve member has a closed first end and an open second end and defines an enclosed interior volume accessible via the open second end. A clip member is configured to be operatively connected to the first or second ear tube. The head and the interconnecting elongate tubular body portion of the stethoscope are reposed in a position in the interior volume of the sleeve member such that the head and the body portion of the stethoscope are substantially covered. The clip member releasably holds the sleeve member in the position.

A method is also provided for protecting a stethoscope including a head to be placed during use in juxtaposition to a patient, first and second ear tubes, and an elongate tubular body portion extending between and interconnecting the head and the ear tubes. The method for protecting the stethoscope comprises the steps of providing an elongate sleeve member having a closed first end and an open second end forming a mouth. The sleeve member defines an enclosed interior volume accessible via the mouth and of sufficient size to allow the head of the stethoscope to be placed therein. The sleeve has a sufficient length to envelope the head end and the tubular body portion of the stethoscope up to at least about the ear tubes. The sleeve is comprised of acoustically transparent, biologically impermeable material. The next step is inserting the head and the interconnecting elongate tubular body portion of the stethoscope in a position in the interior volume of the sleeve member such that the head and the body portion of the stethoscope are substantially covered. The sleeve member is releasably secured in the position with a clip member adapted to be operatively connected to the first or second ear tube. The sleeve member is used on the stethoscope to isolate the patient and the user from passing any contamination between them through mutual contact with the stethoscope while the stethoscope is in use on the patient.

BRIEF DESCRIPTION OF THE DRAWINGS

For a more complete understanding of the stethoscope cover, reference should now be had to the embodiments shown in the accompanying drawings and described below. In the drawings.

DESCRIPTION

Certain terminology is used herein for convenience only and is not to be taken as a limiting. For example, words such as "upper," "lower," "left," "right," "horizontal," "vertical," "upward," "downward," "top" and "bottom" merely describe the configurations shown in the FIGs. Indeed, the components may be oriented in any direction and the terminology, therefore, should be understood as encompassing such variations unless specified otherwise. The words "interior" and "exterior" refer to directions toward and away from, respectively, the geometric center of the core and designated parts thereof. The terminology includes the words specifically mentioned above, derivatives thereof and words of similar import.

Figure 1:
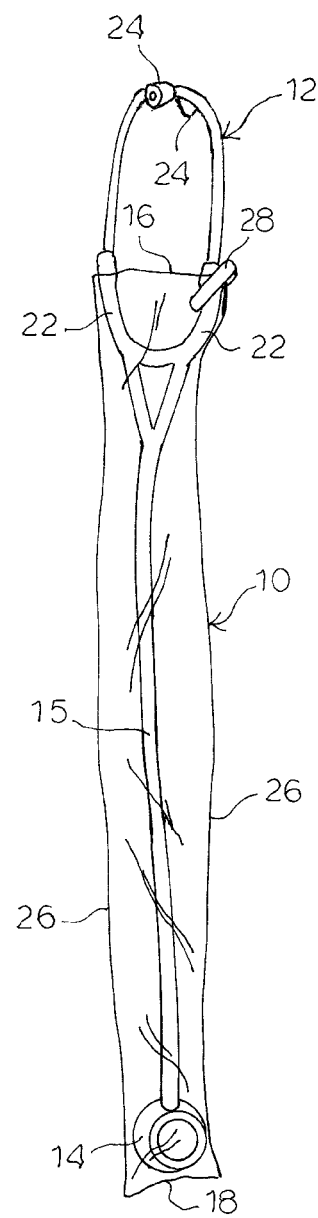
FIG. 1 is an elevation view of an embodiment of a stethoscope sleeve for covering a portion of a stethoscope.
Figure 2:
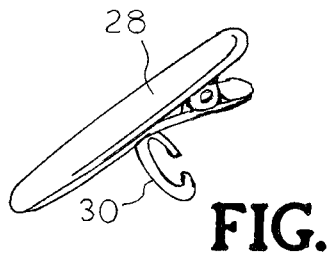
FIG. 2 is a perspective view of an embodiment of a clip for use with the sleeve for covering a stethoscope as shown in FIG. 1.

Referring now to the drawings, wherein like reference numerals designate corresponding or similar elements throughout the several views, an embodiment of a sleeve for covering a standard stethoscope 12 is shown in FIG. 1 and generally designated at 10. The stethoscope 12 to which the sleeve 10 is advantageously applied may be of any suitable type and may be of conventional form, including a head 14 and a flexible sound tube 15 connecting the head 14 to binaural earpiece tubes 22 and ear tips 24. The sleeve 10 is configured to envelop the head 14 of the stethoscope 14 with full covering extending up to cover the sound tube 15 to the junction with the earpiece tubes 22. An upper end 16 of the sleeve 10 is removably affixed to one of the earpiece tubes 22 of the stethoscope 12. The sleeve 10 provides a protective cover for enclosing portions of the stethoscope 12 and is configured to maintain a sterile barrier, thereby isolating the stethoscope 12 from direct contact with both the user as well as the patient for preventing contamination and reducing any risk of infection. The sleeve is designed to fit over all models of off-the-shelf stethoscopes.

Referring to FIG. 1 the sleeve 10 comprises an elongated tubular flexible sheath 18 having a first end 16 and a second end 18. The sleeve 10 has formed therein a cavity defining an enclosed interior volume with an opening at the first end 16 for receiving and at least partially enclosing the head 14 and the center sound tube 15 at the lower end of the stethoscope 12. The sleeve is closed at the second end 18. The first end 16 may be closed by any method or technique known in the art, such as heating sealing, RF sealing, ultrasonic welding, or adhesive bonding. Alternatively, the closed end 16 may be formed by simply folding an elongate strip of polymeric film and sealing such film at its two longitudinal sides, so that the folding edge of such film naturally forms the closed end 16. The longitudinal sides 26 of the sleeve 10 can be formed either with seam lines or without seam lines. The sleeve 10 is sized such that the head 14 of the stethoscope 12 and at least a portion of the sound tube 20 is enveloped by the sleeve 10. In another embodiment shown in FIG. 3, the dimensions of the sleeve may variable as long as the sheath is appropriate for receiving at least the head 14 of the stethoscope 12.

The sleeve 10 may be formed of any substantially flexible material, preferably comprising a material that is acoustically transmitting and impermeable to bacteria, viruses and fluids. For example, the protective cover can be formed of a suitable thermoplastic polymeric material, such as a thin, flexible, polymeric material does not significantly impede or degrade the fidelity of sound transmission to the stethoscope. Suitable materials for the sleeve 10 include polypropylene, polyethylene, latex rubber, silicone, soft vinyl, urethane, as well as fluid, bacterial, and virally impermeable fabric, paper, or the like. Various methods known in the art can be employed to form closure at the second end 18 of the sleeve 10. Such methods include, but are not limited to, heat sealing, radio-frequency sealing, ultrasonic welding, and adhesive bonding. While the sleeve 10 does not have to be sterile, the sleeve may be provided using any suitable sterilization method known for disposable, plastic medical or surgical supplies (e.g., radiation, ethylene oxide, etc.).

Figure 3:
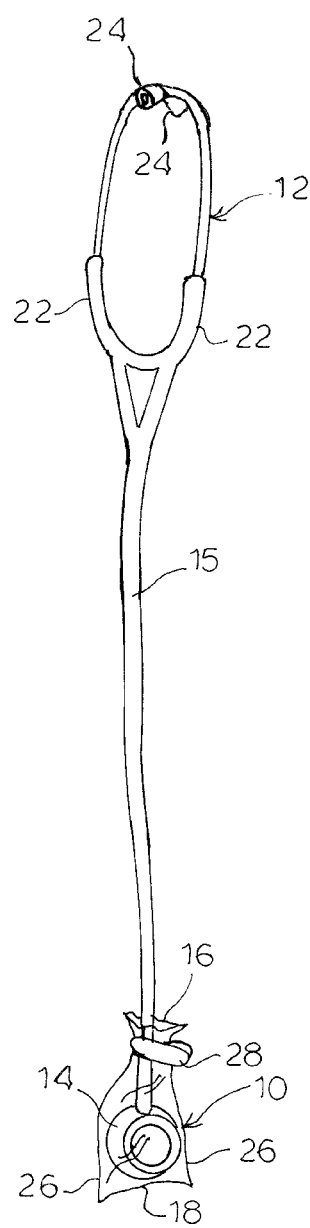
FIG. 3 is an elevation of an embodiment of a stethoscope sleeve for cover a portion of a stethoscope.

Although FIGS. 1 and 3 show a sleeve 10 having a generally rectangular shape, the sleeve 10 can be of any other suitable shape, such as square, trapezium, truncated ellipse with flat ends, etc. The open end 16 of the sleeve 10 can be either longer than the closed end 18, or shorter than the closed end 18. The two longitudinal sides 26 of the sleeve 10 can either be either straight, or curved, with a concave or a convex shape. Multiple variations in respect to the shape of the sleeve 10 can be readily determined by one skilled in the art without undue experimentation and are within the scope and spirit of the present application.

In order to secure the sleeve 10 in a position enveloping the stethoscope 12 during patient examination and prevent potential contamination caused by dropping of the sleeve 10, means are provided for removably securing the sleeve 10 to the stethoscope 12 such that the sleeve is temporarily secured during patient examination and can be readily removed from the stethoscope 12 after the examination is completed. The securing means preferably comprises a clip 28 and a retaining ring 30. The clip 28 may be a compressible clip that can be readily clipped onto the sleeve 10. The retaining ring 30 is mounted to the clip 28. The retaining ring 30 is a generally cylindrical body defining an interior configured to snugly receive a portion of the earpiece tube 22 of the stethoscope 12. The retaining ring 30 is formed from a resilient material such that the ring can plastically deform to accept the earpiece tube 22 through its channel for resiliently securing the ring 30 and the clip 28 on the earpiece tube 22. The ring 30 is configured such that the associated clip 28 extends radially outwardly from the earpiece tube 22. It is to be understood that the retaining ring 30 may be fabricated from any suitable material and may be closed about the earpiece tube 22 in any other fashion, such as by bending the ring 30 around the tube or using hook and loop material, without departing from the scope of the present invention.

The clip 28 is used to compressively releasably secure the free open end 16 of the sleeve 10 to either earpiece tube 22 to prevent the sleeve 10 from being detached from the stethoscope 12 during patient examination. In another embodiment, the clip may include a hook member such that the user could pull the sleeve 10 over the hook for securing the sleeve 10. The hook can perforate the sleeve 10, but it is not necessary as long as the sleeve 10 is secured in position covering the stethoscope 12.

In use, one merely affixes the sleeve 10 about the stethoscope 12, utilizes the stethoscope 12 in a normal fashion, and removes and disposes of the sleeve 10 prior to utilization upon another. More particularly, the head 14 and the sound tube 15 is inserted into the cavity formed in the sleeve 10 until the head 14 contacts the second closed end 18 of sleeve 10, and the first open end 16 of the sleeve 10 is adjacent the earpiece tubes 22. The retaining ring 30 is mounted to the earpiece tube 22 of the stethoscope 12 by forcing the earpiece tube through the channel of the ring into the interior of the ring 30 or by bending the ring 30 around the earpiece tube 22. The sleeve 10 is mounted to the stethoscope 12 by inserting the head 14 of the stethoscope 12 through the open end 16 of the sleeve 10 to the closed end 18. The sleeve 10 surrounds the stethoscope 12. FIG. 1 shows a protectively covered stethoscope 12 with the head 14 and the elongate sound tube 15 portion of the stethoscope 12 disposed in the interior volume of the sleeve 12 while the two earpiece tubes 22 stethoscope are exposed. In a second embodiment of the sleeve 10 as shown in FIG. 3, the sleeve 10 receives only the head 14 of the stethoscope 12. In such manner, the stethoscope is protectively covered and effectively isolated from bio-contaminants.

Once the sleeve 10 is installed about the stethoscope 12, the user may utilize the stethoscope in normal fashion, placing the ear cups in the appropriate position and listening to the patient by grasping the head 14 and applying the head 14 to the desired area.

After using the stethoscope 12 on a patient, the user may remove the sleeve 10 by simply decompressing the clip 28 and pulling the sleeve 10 off of the sound tube 14 and head 14 of the stethoscope 12, disposing of the sleeve 10 thereafter. Even though utilized in examining the patient, the head 14 and sound tube 15 of the stethoscope 12 have not been in contact with the examined patient because of the presence of the sleeve 10, and thereby they remain uncontaminated and safe for use again with the next patient. The clip 28 remains of the stethoscope for releasably securing another unused sleeve 10 installed prior to the next examination.

The stethoscope sleeve as described herein minimizes the risk of transmission of infection from one patient to another via a contaminated stethoscope by isolating the stethoscope in a disposable, biologically impermeable sleeve 10 which may be removed and changed between examinations.

Although a disposable stethoscope cover has been shown and described in considerable detail with respect to only a few exemplary embodiments thereof, it should be understood by those skilled in the art that I do not intend to be limited to the embodiments since various modifications, omissions and additions may be made to the disclosed embodiments without materially departing from the novel teachings and advantages of the stethoscope cover, particularly in light of the foregoing teachings. For example, the clip may be used to mount other objects, such as name tags, pens, pencils, other medical or non-medical accessories, and the like. Accordingly, I intend to cover all such modifications, omission, additions and equivalents as may be included within the spirit and scope of the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

I claim:

1. A protective cover for a stethoscope including a head, first and second ear tubes, and an elongate tubular body portion extending between and interconnecting the head and the ear tubes, the protective cover comprising:
   an elongate sleeve member having a closed first end and an open second end, the sleeve member defining an enclosed interior volume accessible via the open second end; and
   a clip member adapted to be operatively connected to one of the first and second ear tubes,
wherein the head and the interconnecting elongate tubular body portion and at least a portion of the first and second ear tubes of the stethoscope are reposed in a position in the interior volume of the sleeve member such that the head and the body portion and at least a portion of the first and second ear tubes of the stethoscope are substantially covered, and wherein the clip member releasably holds the sleeve member in the position on one of the first and second ear tubes for removal of the sleeve member after use.

2. The protective cover of claim 1, wherein the sleeve member is formed of a material that is acoustically transmissive and impermeable to viruses, bacteria, and fluids.

3. The protective cover of claim 1, wherein the sleeve member is formed of a thermoplastic polymeric material.

4. The protective cover of claim 1, wherein the clip member comprises a ring member adapted to be secured to the first or second ear tube.

5. The protective cover of claim 1, wherein the clip member comprises a ring member adapted to be secured to the tubular body portion, and wherein the head of the stethoscope is reposed in a position in the interior volume of the sleeve member such that the head of the stethoscope is substantially covered.

6. A protectively covered stethoscope assembly comprising:
   a stethoscope including a head, first and second ear tubes, and an elongate tubular body portion extending between and interconnecting the head and the ear tubes;
   an elongate sleeve member having a closed first end and an open second end, the sleeve member defining an enclosed interior volume accessible via the open second end; and
   a clip member operatively connected to one of the first and second ear tubes,
wherein the head and the interconnecting elongate tubular body portion and at least a portion of the first and second ear tubes of the stethoscope are reposed in a position in the interior volume of the sleeve member such that the head and the body portion and at least a portion of the first and second ear tubes of the stethoscope are substantially covered, and wherein the clip member releasably holds the sleeve member in the position on one of the first and second ear tubes for removal of the sleeve member after use.

7. The protective stethoscope assembly of claim 6, wherein the sleeve member is formed of a material that is acoustically transmissive and impermeable to viruses, bacteria, and fluids.

8. The protective stethoscope assembly of claim 6, wherein the sleeve member is formed of a thermoplastic polymeric material.

9. The protective stethoscope assembly of claim 6, wherein the clip member comprises a ring member secured to the first or second ear tube.

10. The protective stethoscope assembly of claim 6, wherein the clip member comprises a ring member secured to the tubular body portion, and wherein the head of the stethoscope is reposed in a position in the interior volume of the sleeve member such that the head of the stethoscope is substantially covered.

11. A method for protecting a stethoscope including a head to be placed during use in juxtaposition to a patient, first and second ear tubes, and an elongate tubular body portion extending between and interconnecting the head and the ear tubes, the method for protecting the stethoscope comprising the steps of:
   providing an elongate sleeve member having a closed first end and an open second end forming a mouth, the sleeve member defining an enclosed interior volume accessible via the mouth and of sufficient size to allow the head of the stethoscope to be placed therein, the sleeve having a sufficient length to envelope the head end and the tubular body portion of the stethoscope up to at least about a portion of the ear tubes, the sleeve being comprised of acoustically transparent, biologically impermeable material;
   inserting the head and the interconnecting elongate tubular body portion and at least a portion of the first and second ear tubes of the stethoscope in a position in the interior volume of the sleeve member such that the head and the body portion and at least a portion of the first and second ear tubes of the stethoscope are substantially covered; and releasably securing the sleeve member in the position with a clip member adapted to be operatively connected to one of the first and second ear tubes; and using the sleeve member on the stethoscope to isolate the patient and the user from passing any contamination between them through mutual contact with the stethoscope while the stethoscope is in use on the patient; and removing the sleeve member after use.

12. The stethoscope protection method of claim 11, further comprising the steps of releasing the sleeve member from the clip member after use on the patient, and removing the stethoscope form the sleeve member.

\* \* \* \* \*